(12) United States Patent
Jonas et al.

(10) Patent No.: US 6,495,554 B2
(45) Date of Patent: Dec. 17, 2002

(54) THIENOPYRIMIDINES

(75) Inventors: Rochus Jonas, Darmstadt (DE); Pierre Schelling, Darmstadt (DE); Franz-Werner Kluxen, Darmstadt (DE); Maria Christadler, Darmstadt (DE)

(73) Assignee: Merck Patent Gesellschaft mit beschraenkter Haftung, Darmstadt (DE)

( * ) Notice: Subject to any disclaimer, the term of this patent is extended or adjusted under 35 U.S.C. 154(b) by 0 days.

(21) Appl. No.: 10/146,028

(22) Filed: May 16, 2002

(65) Prior Publication Data

US 2002/0132818 A1 Sep. 19, 2002

Related U.S. Application Data

(62) Division of application No. 09/555,210, filed as application No. PCT/EP98/07436 on Nov. 19, 1998, now Pat. No. 6,420,368.

(30) Foreign Application Priority Data

Nov. 28, 1997 (DE) .......................... 187 52 852

(51) Int. Cl.⁷ .......................................... A61K 31/5025
(52) U.S. Cl. ...................................... 514/258; 514/267
(58) Field of Search ................................ 514/258, 267

(56) References Cited

FOREIGN PATENT DOCUMENTS

| DE | 245666 | 5/1987 |
|----|--------|--------|
| EP | 0728759 | 8/1996 |
| WO | 9428902 | 12/1994 |
| WO | 9817668 | 4/1998 |

OTHER PUBLICATIONS

Pech, R. et al. "New thieno compounds. Part 12. Prepartion of 4–amino substituted thieno 2,3–d!pyrimidin–2–ylacetic acid derivatives" Pharmazie (1992), 47(1), 20–21.

*Primary Examiner*—John M. Ford
(74) *Attorney, Agent, or Firm*—Millen, White, Zelano & Branigan, P.C.

(57) ABSTRACT

The thienopyrimidines of the formula (I) and their physiologically compatible salts display a phosphodiesterase V inhibiting activity and can be used for treating diseases of the cardiovascular system and for treatment and/or therapy of erectile dysfunction.

12 Claims, No Drawings

THIENOPYRIMIDINES

This application is divisional of U.S. Ser. No. 09/555,210 filed May 26, 2000, now U.S. Pat. No. 6,420,368, which is a 371 of PCT/EP98/07436 filed Nov. 19, 1998.

The invention relates to compounds of the formula I

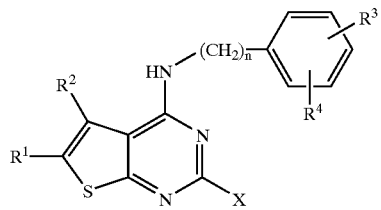

in which
R$^1$, R$^2$ in each case independently of one another are H, A or Hal, where one of the radicals R$^1$ or R$^2$ is always ≠H,
R$^1$ and R$^2$ together are also alkylene having 3–5 C atoms,
R$^3$, R$^4$ in each case independently of one another are H, A, OA or Hal,
R$^3$ and R$^4$ together are also alkylene having 3–5 C atoms, —O—CH$_2$—CH$_2$—, —O—CH$_2$—O— or —O—CH$_2$—CH$_2$—O—,
X is R$^5$ or R$^6$, which is monosubstituted by R$^7$,
R$^5$ is linear or branched alkylene having 1–10 C atoms, in which one or two CH$_2$ groups can be replaced by —CH=CH— groups, or is —C$_6$H$_4$—(CH$_2$)$_m$—,
R$^6$ is cycloalkylalkylene having 6–12 C atoms,
R$^7$ is COOH, COOA, CONH$_2$, CONHA, CON(A)$_2$ or CN,
A is alkyl having 1 to 6 C atoms,
Hal is F, Cl, Br or I,
m is 1 or 2, and
n is 0, 1, 2 or 3,
and their physiologically acceptable salts.

Pyrimidine derivatives are disclosed, for example, in EP 201 188 or WO 93/06104.

The invention is based on the object of finding novel compounds having valuable properties, in particular those which can be used for the production of medicaments.

It has been found that the compounds of the formula I and their salts have very valuable pharmacological properties together with good tolerability.

In particular, they show a specific inhibition of cGMP phosphodiesterase (PDE V).

Quinazolines having cGMP phosphodiesterase-inhibiting activity are described, for example, in J. Med. Chem. 36, 3765 (1993) and ibid. 37, 2106 (1994).

The biological activity of the compounds of the formula I can be determined by methods such as are described, for example, in WO 93/06104. The affinity of the compounds according to the invention for cGMP and cAMP phosphodiesterase is determined by ascertaining their IG$_{50}$ values (concentration of the inhibitor which is needed in order to achieve a 50% inhibition of the enzyme activity). To carry out the determinations, enzymes isolated by known methods can be used (e.g. W. J. Thompson et al., Biochem. 1971, 10, 311). To carry out the experiments, a modified "batch" method of W. J. Thompson and M. M. Appleman (Biochem. 1979, 18, 5228) can be used.

The compounds are therefore suitable for the treatment of disorders of the cardiovascular system, in particular of cardiac insufficiency, and for the treatment and/or therapy of potency disorders (erectile dysfunction).

The use of substituted pyrazolopyrimidinones for the treatment of impotence is described, for example, in WO 94/28902.

The compounds are effective as inhibitors of phenylephrine-induced contractions in cavernous body preparations of hares. This biological action can be demonstrated, for example, by the method which is described by F. Holmquist et al. in J. Urol., 150, 1310–1315 (1993). The inhibition of the contraction shows the efficacy of the compounds according to the invention for the therapy and/or treatment of potency disorders.

The compounds of the formula I can be employed as pharmaceutical active compounds in human and veterinary medicine. They can furthermore be employed as intermediates for the production of further pharmaceutical active compounds.

The invention accordingly relates to the compounds of the formula I and to a process for the preparation of compounds of the formula I according to claim 1, and their salts, characterized in that a) a compound of the formula II

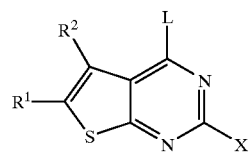

in which
R$^1$, R$^2$ and X have the meanings indicated,
and L is Cl, Br, OH, SCH$_3$ or a reactive esterified OH group,
is reacted with a compound of the formula III

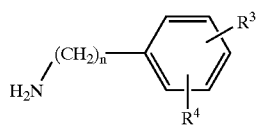

in which
R$^3$, R$^4$ and n have the meanings indicated, or b) a radical X in a compound of the formula I is converted into another radical X by, for example, hydrolysing an ester group to a COOH group or converting a COOH group into an amide or into a cyano group
and/or by converting a compound of the formula I into one of its salts.

Above and below, the radicals R$^1$, R$^2$, R$^3$, R$^4$, R$^5$, R$^6$, R$^7$, X, L and n have the meanings indicated in the formulae I, II and III, if not expressly stated otherwise.

A is alkyl having 1–6 C atoms. In the above formulae, alkyl is preferably unbranched and has 1, 2, 3, 4, 5 or 6 C atoms and is preferably methyl, ethyl or propyl, furthermore preferably isopropyl, butyl, isobutyl, sec-butyl or tert-butyl, but also n-pentyl, neopentyl, isopentyl or hexyl.

X is an R$^5$ or R$^6$ radical which is monosubstituted by R$^7$.

R$^5$ is a linear or branched alkylene radical having 1–10, preferably 1–8, C atoms, the alkylene radical preferably being, for example, methylene, ethylene, propylene, isopropylene, butylene, isobutylene, sec-butylene, pentylene, 1-, 2- or 3-methylbutylene, 1,1-, 1,2- or 2,2- dimethylpropylene, 1-ethylpropylene, hexylene, 1-, 2-, 3- or 4-methylpentylene, 1,1-, 1,2-, 1,3-, 2,2-, 2,3- or 3,3-dimethylbutylene, 1- or 2-ethylbutylene, 1-ethyl-1-methylpropylene, 1-ethyl-2-methylpropylene, 1,1,2- or 1,2,2-trimethylpropylene, linear or branched heptylene, octylene, nonylene or decylene. $R^5$ is furthermore, for example, but-2-enylene or hex-3-enylene.

$R^6$ is cycloalkylalkylene having 6–12 C atoms, preferably, for example, cyclopentylmethylene, cyclohexylmethylene, cyclohexylethylene, cyclohexylpropylene or cyclohexylbutylene.

One of the radicals $R^1$ and $R^2$ is preferably H, while the other is preferably propyl or butyl, but particularly preferably ethyl or methyl. Furthermore, $R^1$ and $R^2$ are also together preferably propylene, butylene or pentylene.

Hal is preferably F, Cl or Br, but also I.

The radicals $R^3$ and $R^4$ can be identical or different and are preferably in the 3- or 4-position of the phenyl ring. They are, for example, in each case independently of one another, H, alkyl, F, Cl, Br or I or together alkylene, such as, for example, propylene, butylene or pentylene, furthermore ethylenoxy, methylenedioxy or ethylenedioxy. Preferably, they are also in each case alkoxy, such as, for example, methoxy, ethoxy or propoxy.

The radical $R^7$ is preferably, for example, COOH, COOCH$_3$, COOC$_2$H$_5$, CONH$_2$, CON(CH$_3$)$_2$, CONHCH$_3$ or CN.

It applies to the entire invention that all radicals which occur a number of times can be identical or different, i.e. are independent of one another.

Accordingly, the invention relates in particular to those compounds of the formula I in which at least one of the radicals mentioned has one of the preferred meanings indicated above. Some preferred groups of compounds can be expressed by the following subformulae Ia to Id, which correspond to the formula I and in which the radicals not designated in greater detail have the meaning indicated in the formula I, but in which in Ia X is $R^5$ or $R^6$, which is substituted by COOH or COOA;

in Ib $R^1$, $R^2$ in each case independently of one another are H, A or Hal, where at least one of the radicals $R^1$ and $R^2$ is always ≠H, $R^3$ and $R^4$ together are alkylene having 3–5 C atoms, —O—CH$_2$—CH$_2$—, —O—CH$_2$—O— or —O—CH$_2$—CH$_2$—O, X is $R^5$ or $R^6$, which is substituted by COOH or COOA;

in Ic $R^1$, $R^2$ in each case independently of one another are H, A or Hal, where at least one of the radicals $R^1$ and $R^2$ is always ≠H, $R^3$, $R^4$ in each case independently of one another are H, A, OA or Hal, $R^3$ and $R^4$ together are alkylene having 3–5 C atoms, —O—CH$_2$—CH$_2$—, —O—CH$_2$— or —O—CH$_2$—CH$_2$—O, X is $R^5$ or $R^6$, which is substituted by COOH or COOA, n is 1 or 2, in Id $R^1$, $R^2$ in each case independently of one another are H, A or Hal, where one of the radicals $R^1$ and $R^2$ is always ≠H, $R^1$ and $R^2$ together are also alkylene having 3–5 C atoms, $R^3$, $R^4$ in each case independently of one another are H, A, OA or Hal, $R^3$ and $R^4$ together are also —O—CH$_2$—O—, X is $R^5$ which is monosubstituted by $R^7$, $R^5$ is linear or branched alkylene having 1 to 10 C atoms, or —C$_6$H$_4$—CH$_2$—, $R^7$ is COOH or COOA, A is alkyl having 1 to 6 C atoms, Hal is F, Cl, Br or I, m is 1 and n is 1 or 2.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the reactions mentioned. Use can also be made in this case of variants which are known per se, which are not mentioned here in greater detail.

In the compounds of the formula II or III, $R^1$, $R^2$, $R^3$, $R^4$, X and n have the meanings indicated, in particular the preferred meanings indicated.

If L is a reactive esterified OH group, this is preferably alkylsulfonyloxy having 1–6 C atoms (preferably methylsulfonyloxy) or arylsulfonyloxy having 6–10 C atoms (preferably phenyl- or p-tolylsulfonyloxy, furthermore also 2-naphthalenesulfonyloxy)).

The compounds of the formula I can preferably be obtained by reacting compounds of the formula II with compounds of the formula III.

If desired, the starting substances can also be formed in situ such that they are not isolated from the reaction mixture, but immediately reacted further to give the compounds of the formula I.

On the other hand, it is possible to carry out the reaction stepwise.

As a rule, the starting compounds of the formulae II and III are known. If they are not known, they can be prepared by methods known per se.

Compounds of the formula II can be obtained, for example, by reaction with POCl$_3$ of compounds which are synthesized from thiophene derivatives and CN-substituted alkylenecarboxylic acid esters (Eur. J. Med. Chem. 23, 453 (1988)).

In detail, the reaction of the compounds of the formula II with the compounds of the formula III is carried out in the presence or absence of an inert solvent at temperatures between approximately −20 and approximately 150°, preferably between 20 and 100°.

The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylamine, pyridine or quinoline or of an excess of the amine component, can be favourable.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxane, glycol ethers such as ethylene glycol monomethyl or monoethyl ether (methyl glycol or ethyl glycol), ethylene glycol dimethyl ether (diglyme); ketones such as acetone or butanone; amides such as acetamide, dimethylacetamide, N-methylpyrrolidone or dimethylformamide (DMF); nitriles such as acetonitrile; sulfoxides such as dimethyl sulfoxide (DMSO); nitro compounds such as nitromethane or nitrobenzene; esters such as ethyl acetate or mixtures of the solvents mentioned.

It is furthermore possible, in a compound of the formula I, to convert a radical X into another radical X, e.g. by hydrolysing an ester or a cyano group to a COOH group.

Ester groups can be hydrolysed, for example, using NaOH or KOH in water, water-THF or water-dioxane at temperatures between 0 and 100° C.

Carboxylic acids can be converted into the corresponding carbonyl chlorides, for example, using thionyl chloride and these can be converted into carboxamides. Carbonitriles are obtained from these by elimination of water in a known manner.

An acid of the formula I can be converted into the associated acid addition salt using a base, for example by reaction of equivalent amounts of the acid and of the base in an inert solvent such as ethanol and subsequent evaporation. Possible bases for this reaction are those which yield physiologically acceptable salts. Thus the acid of the formula I can be converted into the corresponding metal salt, in particular alkali metal or alkaline earth metal salt, or into the corresponding ammonium salt using a base (e.g. sodium or potassium hydroxide or carbonate). Possible bases for this reaction are, in particular, also organic bases which yield physiologically acceptable salts, such as, for example, ethanolamine.

On the other hand, a base of the formula I can be converted into the associated acid addition salt using an acid, for example by reaction of equivalent amounts of the base and of the acid in an inert solvent such as ethanol and subsequent evaporation. Possible acids for this reaction are in particular those which yield physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, e.g. picrates, can be used for the isolation and/or purification of compounds of the formula I.

The invention furthermore relates to the use of the compounds of the formula I and/or their physiologically acceptable salts for the production of pharmaceutical preparations, in particular in a non-chemical way. In this case, they can be brought into a suitable dose form together with at least one solid, liquid and/or semi-liquid excipient or auxiliary and, if appropriate, in combination with one or more further active compounds.

The invention also relates to medicaments of the formula I and their physiologically acceptable salts as phosphodiesterase V inhibitors.

The invention furthermore relates to pharmaceutical preparations comprising at least one compound of the formula I and/or one of its physiologically acceptable salts.

These preparations can be used as pharmaceuticals in human or veterinary medicine. Possible excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glyceryl triacetates, gelatin, carbohydrates such as lactose or starch, magnesium stearate, talc, petroleum jelly. Tablets, pills, coated tablets, capsules, powders, granules, syrups, juices or drops are used, in particular, for oral administration, suppositories are used for rectal administration, solutions, preferably oily or aqueous solutions, furthermore suspensions, emulsions or implants, are used for parenteral administration, and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colourants, flavourings and/or one or more further active compounds, e.g. one or more vitamins.

The compounds of the formula I and their physiologically acceptable salts can be employed in the control of diseases in which an increase in cGMP (cyclic guanosine monophosphate) leads to inhibition or prevention of inflammation and muscle relaxation. The compounds according to the invention can be used in particular in the treatment of diseases of the cardiovascular system and for the treatment and/or therapy of potency disorders.

In this case, as a rule the substances are preferably administered in doses of between approximately 1 and 500 mg, in particular between 5 and 100 mg, per dose unit. The daily dose is preferably between approximately 0.02 and 10 mg/kg of body weight. The specific dose for each patient depends, however, on all sorts of factors, for example on the efficacy of the specific compound employed, on the age, body weight, general state of health, sex, on the diet, on the time and route of administration, and on the excretion rate, pharmaceutical combination and severity of the respective disorder to which the therapy applies. Oral administration is preferred.

Above and below, all temperatures are indicated in ° C. In the following examples, "customary working up" means: water is added, if necessary, the mixture is adjusted, if necessary, to pHs of between 2 and 10 depending on the constitution of the final product and extracted with ethyl acetate or dichloromethane, the organic phase is separated off, dried over sodium sulfate and evaporated, and the residue is purified by chromatography on silica gel and/or by crystallization.

Mass spectrometry (MS): EI (electron impact ionization) M$^+$ FAB (fast atom bombardment) (M+H)$^+$

EXAMPLE 1

1.9 g of methyl 3-(4-chloro-5,6,7,8-tetrahydro-[1]benzothieno[2,3-d]pyrimidin-2-yl)propionate [obtainable by cyclization of methyl 2-amino-4,5,6,7-tetrahydrobenzothiophene-3-carboxylate with methyl 3-cyanopropionate and subsequent chlorination with phosphorus oxychloride/dimethylamine] and 2.3 g of 3-chloro-4-methoxybenzylamine ("A") in 20 ml of N-methylpyrrolidone are stirred at 110° for 5 hours. The solvent is removed and worked up in the customary manner. 2.6 g of methyl 3-[4-(3-chloro-4-methoxybenzylamino)-5,6,7,8-tetrahydro[1]benzothieno-[2,3-d]pyrimidin-2-yl]propionate are obtained as a colourless oil.

The following are obtained analogously by reaction of "A"

with methyl 3-(4-chloro-5,6-cyclopenteno[1]benzothieno[2,3-d]pyrimidin-2-yl)propionate
methyl 3-[4-(3-chloro-4-methoxybenzylamino)-5,6-cyclopenteno[1]benzothieno[2,3-d]pyrimidin-2-yl]propionate;

with methyl 3-(4-chloro-5,6-cyclopenteno[1]benzothieno[2,3-d]pyrimidin-2-yl)propionate
methyl 3-[4-(3-chloro-4-methoxybenzylamino)-5,6-cyclopenteno[1]benzothieno[2,3-d]pyrimidin-2-yl]propionate;

with methyl 3-(4-chloro-6-methylthieno[2,3-d]pyrimidin-2-yl)propionate
methyl 3-[4-(3-chloro-4-methoxybenzylamino)-6-methylthieno[2,3-d]pyrimidin-2-yl]propionate;

with methyl 3-(4-chloro-5,6-dimethylthieno[2,3-d]pyrimidin-2-yl)propionate
methyl 3-[4-(3-chloro-4-methoxybenzylamino)-5,6-dimethylthieno[2,3-d]pyrimidin-2-yl]propionate;

with methyl 3-(4-chloro-6-ethylthieno[2,3-d]pyrimidin-2-yl)propionate
methyl 3-[4-(3-chloro-4-methoxybenzylamino)-6-ethylthieno[2,3-d]pyrimidin-2-yl]propionate;

with methyl 3-(4,6-dichlorothieno[2,3-d]pyrimidin-2-yl)propionate
methyl 3-[4-(3-chloro-4-methoxybenzylamino)-6-chlorothieno[2,3-d]pyrimidin-2-yl]propionate;

with methyl 2-(4-chloro-5,6,7,8-tetrahydro[1]benzothieno[2,3-d]pyrimidin-2-yl)acetate
methyl 2-[4-(3-chloro-4-methoxybenzylamino)-5,6,7,8-tetrahydro[1]benzothieno[2,3-d]pyrimidin-2-yl]acetate.

The following are obtained analogously by reaction of 3,4-methylenedioxybenzylamine with methyl 3-(4-chloro-5,6,7,8-tetrahydro[1]benzothieno[2,3-d]pyrimidin-2-yl)propionate
methyl 3-[4-(3,4-methylenedioxybenzylamino)-5,6,7,8-tetrahydro[1]benzothieno[2,3-d]pyrimidin-2-yl]propionate with methyl 3-(4-chloro-5,6-cyclopenteno[1]benzothieno[2,3-d]pyrimidin-2-yl)propionate
methyl 3-[4-(3,4-methylenedioxybenzylamino)-5,6-cyclopenteno[1]benzothieno[2,3-d]pyrimidin-2-yl]propionate;

with methyl 3-(4-chloro-5,6-cyclohepteno[1]benzothieno[2,3-d]pyrimidin-2-yl)propionate
methyl 3-[4-(3,4-methylenedioxybenzylamino)-5,6-cyclohepteno[1]benzothieno[2,3-d]pyrimidin-2-yl]propionate;

with methyl 3-(4-chloro-6-methylthieno[2,3-d]pyrimidin-2-yl)propionate
methyl 3-[4-(3,4-methylenedioxybenzylamino)-6-methylthieno-[2,3-d]pyrimidin-2-yl]propionate;

with methyl 3-(4-chloro-5,6-dimethylthieno[2,3-]pyrimidin-2-yl)propionate
methyl 3-[4-(3,4-methylenedioxybenzylamino)-5,6-dimethylthieno-[2,3-d]pyrimidin-2-yl]propionate;

with methyl 3-(4-chloro-6-ethylthieno[2,3-d]pyrimidin-2-yl)propionate
methyl 3-[4-(3,4-methylenedioxybenzylamino)-6-ethylthieno[2,3-d]pyrimidin-2-yl]propionate;

with methyl 3-(4,6-dichlorothieno[2,3-d]pyrimidin-2-yl)propionate
methyl 3-[4-(3,4-methylenedioxybenzylamino)-6-chlorothieno[2,3-d]pyrimidin-2-yl]propionate.

The following are obtained analogously by reaction of "A"

with methyl 4-(4-chloro-5,6,7,8-tetrahydro[1]benzothieno[2,3-d]pyrimidin-2-yl)butyrate
methyl 4-[4-(3-chloro-4-methoxybenzylamino)-5,6,7,8-tetrahydro[1]benzothieno[2,3-d]pyrimidin-2-yl]butyrate;

with methyl 4-(4-chloro-5,6-cyclopenteno[1]benzothieno[2,3-d]pyrimidin-2-yl)butyrate
methyl 4-[4-(3-chloro-4-methoxybenzylamino)-5,6-cyclopenteno[1]benzothieno[2,3-d]pyrimidin-2-yl]butyrate;

with methyl 4-(4-chloro-5,6-cyclohepteno[1]benzothieno[2,3-d]pyrimidin-2-yl)butyrate
methyl 4-[4-(3-chloro-4-methoxybenzylamino)-5,6-cyclohepteno[1]benzothieno[2,3-d]pyrimidin-2-yl]butyrate;

with methyl 4-(4-chloro-6-methylthieno[2,3-d]pyrimidin-2-yl)butyrate
methyl 4-[4-(3-chloro-4-methoxybenzylamino)-6-methylthieno[2,3-d]pyrimidin-2-yl]butyrate;

with methyl 4-(4-chloro-5,6-dimethylthieno[2,3-d]pyrimidin-2-yl)butyrate
methyl 4-[4-(3-chloro-4-methoxybenzylamino)-5,6-dimethylthieno[2,3-d]pyrimidin-2-yl]butyrate;

with methyl 4-(4-chloro-6-ethylthieno[2,3-d]pyrimidin-2-yl)butyrate
methyl 4-[4-(3-chloro-4-methoxybenzylamino)-6-ethylthieno[2,3-d]pyrimidin-2-yl]butyrate;

with methyl 4-(4,6-chloro-6-chlorothieno[2,3-d]pyrimidin-2-yl)butyrate
methyl 4-[4-(3-chloro-4-methoxybenzylamino)-6-chlorothieno[2,3-d]pyrimidin-2-yl]butyrate.

The following are obtained analogously by reaction of 3,4-methylenedioxybenzylamine with methyl 4-(4-chloro-5,6,7,8-tetrahydro[1]benzothieno[2,3-d]pyrimidin-2-yl)butyrate
methyl 4-[4-(3,4-methylenedioxybenzylamino)-5,6,7,8-tetrahydro[1]benzothieno[2,3-d]pyrimidin-2-yl]butyrate;

with methyl 4-(4-chloro-5,6-cyclopenteno[1]benzothieno[2,3-d]pyrimidin-2-yl)butyrate;
methyl 4-[4-(3,4-methylenedioxybenzylamino)-5,6-cyclopenteno[1]benzothieno[2,3-d]pyrimidin-2-yl]butyrate;

with methyl 4-(4-chloro-5,6-cyclohepteno[1]benzothieno[2,3-d]pyrimidin-2-yl)butyrate
methyl 4-[4-(3,4-methylenedioxybenzylamino)-5,6-cyclohepteno[1]benzothieno[2,3-d]pyrimidin-2-yl]butyrate;

with methyl 4-(4-chloro-6-methylthieno[2,3-d]pyrimidin-2-yl)butyrate
methyl 4-[4-(3,4-methylenedioxybenzylamino)-6-methylthieno[2,3-d]pyrimidin-2-yl]butyrate;

with methyl 4-(4-chloro-5,6-dimethylthieno[2,3-d]pyrimidin-2-yl)butyrate
methyl 4-[4-(3,4-methylenedioxybenzylamino)-5,6-dimethylthieno[2,3-d]pyrimidin-2-yl]butyrate;

with methyl 4-(4-chloro-6-ethylthieno[2,3-d]pyrimidin-2-yl)butyrate
methyl 4-[4-(3,4-methylenedioxybenzylamino)-6-ethylthieno[2,3-d]pyrimidin-2-yl]butyrate;

with methyl 4-(4,6-dichlorothieno[2,3-d]pyrimidin-2-yl)butyrate
methyl 4-[4-(3,4-methylenedioxybenzylamino)-6-chlorothieno[2,3-d]pyrimidin-2-yl]butyrate.

The following are obtained analogously by reaction of "A"
with methyl 5-(4-chloro-5,6,7,8-tetrahydro[1]benzothieno[2,3-d]pyrimidin-2-yl)valerate
  methyl 5-[4-(3-chloro-4-methoxybenzylamino)-5,6,7,8-tetrahydro[1]benzothieno[2,3-d]pyrimidin-2-yl]valerate;
with methyl 5-(4-chloro-5,6-cyclopenteno[1]benzothieno[2,3-d]pyrimidin-2-yl)valerate
  methyl 5-[4-(3-chloro-4-methoxybenzylamino)-5,6-cyclopenteno[1]benzothieno[2,3-d]pyrimidin-2-yl]valerate
with methyl 5-(4-chloro-5,6-cyclohepteno[1]benzothieno[2,3-d]pyrimidin-2-yl)valerate
  methyl 5-[4-(3-chloro-4-methoxybenzylamino)-5,6-cyclohepteno[1]benzothieno[2,3-d]pyrimidin-2-yl]valerate
with methyl 5-(4-chloro-6-methylthieno[2,3-d]pyrimidin-2-yl)valerate
  methyl 5-[4-(3-chloro-4-methoxybenzylamino)-6-methylthieno[2,3-d]pyrimidin-2-yl]valerate;
with methyl 5-(4-chloro-5,6-dimethylthieno-[2,3-d]-2-yl)valerate
  methyl 5-[4-(3-chloro-4-methoxybenzylamino)-5,6-dimethylthieno[2,3-d]pyrimidin-2-yl]valerate;
with methyl 5-(4-chloro-6-ethylthieno[2,3-d]pyrimidin-2-yl)valerate
  methyl 5-[4-(3-chloro-4-methoxybenzylamino)-6-ethylthieno[2,3-d]pyrimidin-2-yl]valerate;
with methyl 5-(4,6-dichlorothieno[2,3-d]pyrimidin-2-yl)valerate
  methyl 5-[4-(3-chloro-4-methoxybenzylamino)-6-chlorothieno[2,3-d]pyrimidin-2-yl]valerate.

The following are obtained analogously by reaction of 3,4-methylenedioxybenzylamine
with methyl 5-(4-chloro-5,6,7,8-tetrahydro[1]benzothieno[2,3-d]pyrimidin-2-yl)valerate
  methyl 5-[4-(3,4-methylenedioxybenzylamino)-5,6,7,8-tetrahydro[1]benzothieno[2,3-d]pyrimidin-2-yl]valerate;
with methyl 5-(4-chloro-5,6-cyclopenteno[1]benzothieno[2,3-d]pyrimidin-2-yl)valerate
  methyl 5-[4-(3,4-methylenedioxybenzylamino)-5,6-cyclopenteno[1]benzothieno[2,3-d]pyrimidin-2-yl]valerate;
with methyl 5-(4-chloro-5,6-cyclohepteno[1]benzothieno[2,3-d]pyrimidin-2-yl)valerate
  methyl 5-[4-(3,4-methylenedioxybenzylamino)-5,6-cyclohepteno[1]benzothieno[2,3-d]pyrimidin-2-yl]valerate;
with methyl 5-(4-chloro-6-methylthieno[2,3-d]pyrimidin-2-yl)valerate
  methyl 5-[4-(3,4-methylenedioxybenzylamino)-6-methylthieno[2,3-d]pyrimidin-2-yl]valerate;
with methyl 5-(4-chloro-5,6-dimethylthieno[2,3-d]pyrimidin-2-yl)valerate
  methyl 5-[4-(3,4-methylenedioxybenzylamino)-5,6-dimethylthieno[2,3-d]pyrimidin-2-yl]valerate
with methyl 5-(4-chloro-6-ethylthieno[2,3-d]pyrimidin-2-yl)valerate
  methyl 5-[4-(3,4-methylenedioxybenzylamino)-6-ethylthieno[2,3-d]pyrimidin-2-yl]valerate;
with methyl 5-(4,6-dichlorothieno[2,3-d]pyrimidin-2-yl)valerate
  methyl 5-[4-(3,4-methylenedioxybenzylamino)-6-chlorothieno[2,3-d]pyrimidin-2-yl]valerate.

The following are obtained analogously by reaction of "A"
with methyl 7-(4-chloro-5,6,7,8-tetrahydro[1]benzothieno[2,3-d]pyrimidin-2-yl)heptanoate
  methyl 7-[4-(3-chloro-4-methoxybenzylamino)-5,6,7,8-tetrahydro[1]benzothieno[2,3-d]pyrimidin-2-yl]heptanoate;
with methyl 7-(4-chloro-5,6-cyclopenteno[1]benzothieno[2,3-d]pyrimidin-2-yl)heptanoate
  methyl 7-[4-(3-chloro-4-methoxybenzylamino)-5,6-cyclopenteno[1]benzothieno[2,3-d]pyrimidin-2-yl]heptanoate;
with methyl 7-(4-chloro-5,6-cyclohepteno[1]benzothieno[2,3-d]pyrimidin-2-yl)heptanoate
  methyl 7-[4-(3-chloro-4-methoxybenzylamino)-5,6-cyclohepteno[1]benzothieno[2,3-d]pyrimidin-2-yl]heptanoate;
with methyl 7-(4-chloro-6-methylthieno[2,3-d]pyrimidin-2-yl)heptanoate
  methyl 7-[4-(3-chloro-4-methoxybenzylamino)-6-methylthieno[2,3-d]pyrimidin-2-yl]heptanoate;
with methyl 7-(4-chloro-5,6-dimethylthieno[2,3-d]pyrimidin-2-yl)heptanoate
  methyl 7-[4-(3-chloro-4-methoxybenzylamino)-5,6-dimethylthieno[2,3-d]pyrimidin-2-yl]heptanoate;
with methyl 7-(4-chloro-6-ethylthieno[2,3-d]pyrimidin-2-yl)heptanoate
  methyl 7-[4-(3-chloro-4-methoxybenzylamino)-6-ethylthieno[2,3-d]pyrimidin-2-yl]heptanoate;
with methyl 7-(4-chloro-6-chlorothieno[2,3-d]pyrimidin-2-yl)heptanoate
  methyl 7-[4-(3-chloro-4-methoxybenzylamino)-6-chlorothieno[2,3-d]pyrimidin-2-yl]heptanoate.

The following are obtained analogously by reaction with 3,4-methylenedioxybenzylamine
with methyl 7-(4-chloro-5,6,7,8-tetrahydro[1]benzothieno[2,3-d]pyrimidin-2-yl)heptanoate
  methyl 7-[4-(3,4-methylenedioxybenzylamino)-5,6,7,8-tetrahydro[1]benzothieno[2,3-d]pyrimidin-2-yl]heptanoate;
with methyl 7-(4-chloro-5,6-cyclopenteno[1]benzothieno[2,3-d]pyrimidin-2-yl)heptanoate
  methyl 7-[4-(3,4-methylenedioxybenzylamino)-5,6-cyclopenteno[1]benzothieno[2,3-d]pyrimidin-2-yl]heptanoate;
with methyl 7-(4-chloro-5,6-cyclohepteno[1]benzothieno[2,3-d]pyrimidin-2-yl)heptanoate
  methyl 7-[4-(3,4-methylenedioxybenzylamino)-5,6-cyclohepteno[1]benzothieno[2,3-d]pyrimidin-2-yl]heptanoate;
with methyl 7-(4-chloro-6-methylthieno[2,3-d]pyrimidin-2-yl)heptanoate
  methyl 7-[4-(3,4-methylenedioxybenzylamino)-6-methylthieno[2,3-d]pyrimidin-2-yl]valerate;
with methyl 7-(4-chloro-5,6-dimethylthieno[2,3-d]pyrimidin-2-yl)heptanoate
  methyl 7-[4-(3,4-methylenedioxybenzylamino)-5,6-dimethylthieno[2,3-d]pyrimidin-2-yl]heptanoate;
with methyl 7-(4-chloro-6-ethylthieno[2,3-d]pyrimidin-2-yl)heptanoate
  methyl 7-[4-(3,4-methylenedioxybenzylamino)-6-ethylthieno[2,3-d]pyrimidin-2-yl]heptanoate;
with methyl 7-(4,6-dichlorothieno[2,3-d]pyrimidin-2-yl)heptanoate
  methyl 7-[4-(3,4-methylenedioxybenzylamino)-6-chlorothieno[2,3-d]pyrimidin-2-yl]heptanoate.

The following are obtained analogously by reaction of "A"

with methyl 2-[4-(4-chloro-5,6,7,8-tetrahydro[1]benzothieno[2,3-d]pyrimidin-2-yl)cyclohex-1-yl]acetate methyl 2-{4-[4-(3-chloro-4-methoxybenzylamino)-5,6,7,8-tetrahydro[1]benzothieno[2,3-d]pyrimidin-2-yl]cyclohex-1-yl}acetate;

with methyl 2-[4-(4-chloro-6-ethylthieno[2,3-d]pyrimidin-2-yl)cyclohex-1-yl]acetate methyl 2-{4-[4-(3-chloro-4-methoxybenzylamino)-6-ethylthieno[2,3-d]pyrimidin-2-yl]cyclohex-1-yl}acetate.

The following are obtained analogously by reaction of 3,4-methylenedioxybenzylamine with methyl 2-[4-(4-chloro-5,6,7,8-tetrahydro[1]benzothieno[2,3-d]pyrimidin-2-yl)cyclohex-1-yl]acetate methyl 2-{4-[4-(3,4-methylenedioxybenzylamino)-5,6,7,8-tetrahydro[1]benzothieno[2,3-d]pyrimidin-2-yl]cyclohex-1-yl}acetate.

The following are obtained analogously by reaction of benzylamine with methyl 3-(4-chloro-5,6,7,8-tetrahydro[1]benzothieno[2,3-d]pyrimidin-2-yl)propionate methyl 3-(4-benzylamino-5,6,7,8-tetrahydro[1]benzothieno[2,3-d]pyrimidin-2-yl)propionate;

with methyl 4-(4-chloro-5,6,7,8-tetrahydro[1]benzothieno[2,3-d]pyrimidin-2-yl)butyrate methyl 4-(4-benzylamino-5,6,7,8-tetrahydro[1]benzothieno[2,3-d]pyrimidin-2-yl)butyrate;

with methyl 5-(4-chloro-5,6,7,8-tetrahydro[1]benzothieno[2,3-d]pyrimidin-2-yl)valerate methyl 5-(4-benzylamino-5,6,7,8-tetrahydro[1]benzothieno[2,3-d]pyrimidin-2-yl)valerate;

with methyl 4-(4-chloro-6-methylthieno[2,3-d]pyrimidin-2-yl)butyrate methyl 4-(4-benzylamino-6-methylthieno[2,3-d]pyrimidin-2-yl)butyrate;

with methyl 5-(4-chloro-6-ethylthieno[2,3-d]pyrimidin-2-yl)valerate methyl 5-(4-benzylamino-6-ethylthieno[2,3-d]pyrimidin-2-yl)valerate.

EXAMPLE 2

2.2 g of methyl 3-[4-(3-chloro-4-methoxybenzylamino)-5,6,7,8-tetrahydro[1]benzothieno[2,3-d]pyrimidin-2-yl]propionate are dissolved in 20 ml of ethylene glycol monomethyl ether and, after addition of 10 ml of 32% NaOH solution, the mixture is stirred at 110° for 5 hours. After addition of 20% HCl, it is extracted with dichloromethane. By addition of petroleum ether, 2.0 g of 3-[4-(3-chloro-4-methoxybenzylamino)-5,6,7,8-tetrahydro[1]benzothieno-[2,3-d]pyrimidin-2-yl]propionic acid, m.p. 229° are obtained.

The deposited crystals are dissolved in 30 ml of isopropanol and treated with 0.5 g of ethanolamine. After crystallization, 1.35 g of 3-[4-(3-chloro-4-methoxybenzylamino)-5,6,7,8-tetrahydro[1]benzothieno[2,3-d]pyrimidin-2-yl]propionic acid, ethanolamine salt, m.p. 135° are obtained.

The carboxylic acids below are obtained analogously from the esters listed under Example 1:

3-[4-(3-chloro-4-methoxybenzylamino)-5,6-cyclopenteno[1]benzothieno[2,3-d]pyrimidin-2-yl]propionic acid;

3-[4-(3-chloro-4-methoxybenzylamino)-5,6-cyclohepteno[1]benzothieno[2,3-d]pyrimidin-2-yl]propionic acid;

3-[4-(3-chloro-4-methoxybenzylamino)-6-methylthieno[2,3-d]pyrimidin-2-yl]propionic acid;

3-[4-(3-chloro-4-methoxybenzylamino)-5,6-methylthieno[2,3-d]pyrimidin-2-yl]propionic acid;

3-[4-(3-chloro-4-methoxybenzylamino)-6-ethylthieno[2,3-d]pyrimidin-2-yl]propionic acid;

3-[4-(3-chloro-4-methoxybenzylamino)-6-chlorothieno[2,3-d]pyrimidin-2-yl]propionic acid;

2-[4-(3-chloro-4-methoxybenzylamino)-5,6,7,8-tetrahydro[1]benzothieno[2,3-d]pyrimidin-2-yl]acetic acid, ethanolamine salt, m.p. 126°;

3-[4-(3,4-methylenedioxybenzylamino)-5,6,7,8-tetrahydro[1]benzothieno[2,3-d]pyrimidin-2-yl]propionic acid;

3-[4-(3,4-methylenedioxybenzylamino)-5,6-cyclopenteno[1]benzothieno[2,3-d]pyrimidin-2-yl]propionic acid;

3-[4-(3,4-methylenedioxybenzylamino)-5,6-cyclohepteno[1]benzothieno[2,3-d]pyrimidin-2-yl]propionic acid;

3-[4-(3,4-methylenedioxybenzylamino)-6-methylthieno[2,3-d]pyrimidin-2-yl]propionic acid;

3-[4-(3,4-methylenedioxybenzylamino)-5,6-dimethylthieno[2,3-d]pyrimidin-2-yl]propionic acid;

3-[4-(3,4-methylenedioxybenzylamino)-6-ethylthieno[2,3-d]pyrimidin-2-yl]propionic acid;

3-[4-(3,4-methylenedioxybenzylamino)-6-chlorothieno[2,3-d]pyrimidin-2-yl]propionic acid;

4-[4-(3-chloro-4-methoxybenzylamino)-5,6,7,8-tetrahydro[1]benzothieno[2,3-d]pyrimidin-2-yl]butyric acid;

4-[4-(3-chloro-4-methoxybenzylamino)-5,6-cyclopenteno[1]benzothieno[2,3-d]pyrimidin-2-yl]butyric acid;

4-[4-(3-chloro-4-methoxybenzylamino)-5,6-cyclohepteno[1]benzothieno[2,3-d]pyrimidin-2-yl]butyric acid;

4-[4-(3-chloro-4-methoxybenzylamino)-6-methylthieno[2,3-d]pyrimidin-2-yl]butyric acid, ethanolamine salt, m.p. 142°;

4-[4-(3-chloro-4-methoxybenzylamino)-5,6-methylthieno[2,3-d]pyrimidin-2-yl]butyric acid;

4-[4-(3-chloro-4-methoxybenzylamino)-6-ethylthieno[2,3-d]pyrimidin-2-yl]butyric acid, ethanolamine salt, m.p. 170°;

4-[4-(3-chloro-4-methoxybenzylamino)-6-chlorothieno[2,3-d]pyrimidin-2-yl]butyric acid;

4-[4-(3,4-methylenedioxybenzylamino)-5,6,7,8-tetrahydro[1]benzothieno[2,3-d]pyrimidin-2-yl]butyric acid, ethanolamine salt, m.p. 114°;

4-[4-(3,4-methylenedioxybenzylamino)-5,6-cyclopenteno[1]benzothieno[2,3-d]pyrimidin-2-yl]butyric acid;

4-[4-(3,4-methylenedioxybenzylamino)-5,6-cyclohepteno[1]benzothieno[2,3-d]pyrimidin-2-yl]butyric acid;

4-[4-(3,4-methylenedioxybenzylamino)-6-methylthieno[2,3-d]pyrimidin-2-yl]butyric acid, ethanolamine salt, m.p. 170°;

4-[4-(3,4-methylenedioxybenzylamino)-5,6-dimethylthieno[2,3-d]pyrimidin-2-yl]butyric acid;

4-[4-(3,4-methylenedioxybenzylamino)-6-ethylthieno[2,3-d]pyrimidin-2-yl]butyric acid;

4-[4-(3,4-methylenedioxybenzylamino)-6-chlorothieno[2,3-d]pyrimidin-2-yl]butyric acid;

5-[4-(3-chloro-4-methoxybenzylamino)-5,6,7,8-tetrahydro[1]benzothieno[2,3-d]pyrimidin-2-yl]valeric acid, m.p. 165°; ethanolamine salt, m.p. 112°;

5-[4-(3-chloro-4-methoxybenzylamino)-5,6-cyclopenteno[1]benzothieno[2,3-d]pyrimidin-2-yl]valeric acid;

5-[4-(3-chloro-4-methoxybenzylamino)-5,6-cyclohepteno[1]benzothieno[2,3-d]pyrimidin-2-yl]valeric acid;

5-[4-(3-chloro4-methoxybenzylamino)-6-methylthieno[2,3-d]pyrimidin-2-yl]valeric acid, ethanolamine salt, m.p. 156°;

5-[4-(3-chloro-4-methoxybenzylamino)-5,6-dimethylthieno[2,3-d]pyrimidin-2-yl]valeric acid;

5-[4-(3-chloro-4-methoxybenzylamino)-6-ethylthieno[2,3-d]pyrimidin-2-yl]valeric acid, ethanolamine salt, m.p. 156°;

5-[4-(3-chloro-4-methoxybenzylamino)-6-chlorothieno[2,3-d]pyrimidin-2-yl]valeric acid;

5-[4-(3,4-methylenedioxybenzylamino)-5,6,7,8-tetrahydro[1]benzothieno[2,3-d]pyrimidin-2-yl]valeric acid;

5-[4-(3,4-methylenedioxybenzylamino)-5,6-cyclopenteno[1]benzothieno[2,3-d]pyrimidin-2-yl]valeric acid;

5-[4-(3,4-methylenedioxybenzylamino)-5,6-cyclohepteno[1]benzothieno[2,3-d]pyrimidin-2-yl]valeric acid;

5-[4-(3,4-methylenedioxybenzylamino)-6-methylthieno[2,3-d]pyrimidin-2-yl]valeric acid, ethanolamine salt, m.p. 167°;

5-[4-(3,4-methylenedioxybenzylamino)-5,6-dimethylthieno[2,3-d]pyrimidin-2-yl]valeric acid;

5-[4-(3,4-methylenedioxybenzylamino)-6-ethylthieno[2,3-d]pyrimidin-2-yl]valeric acid;

5-[4-(3,4-methylenedioxybenzylamino)-6-chlorothieno[2,3-d]pyrimidin-2-yl]valeric acid;

7-[4-(3-chloro-4-methoxybenzylamino)-5,6,7,8-tetrahydro[1]benzothieno[2,3-d]pyrimidin-2-yl]heptanoic acid, ethanolamine salt, m.p. 130°;

7-[4-(3-chloro-4-methoxybenzylamino)-5,6-cyclopenteno[1]benzothieno[2,3-d]pyrimidin-2-yl]heptanoic acid 7-[4-(3-chloro-4-methoxybenzylamino)-5,6-cyclohepteno[1]benzothieno[2,3-d]pyrimidin-2-yl]heptanoic acid;

7-[4-(3-chloro-4-methoxybenzylamino)-6-methylthieno[2,3-d]pyrimidin-2-yl]heptanoic acid;

7-[4-(3-chloro-4-methoxybenzylamino)-5,6-dimethylthieno[2,3-d]pyrimidin-2-yl]heptanoic acid;

7-[4-(3-chloro-4-methoxybenzylamino)-6-ethylthieno[2,3-d]pyrimidin-2-yl]heptanoic acid;

7-[4-(3-chloro-4-methoxybenzylamino)-6-chlorothieno[2,3-d]pyrimidin-2-yl]heptanoic acid;

7-[4-(3,4-methylenedioxybenzylamino)-5,6,7,8-tetrahydro[1]benzothieno[2,3-d]pyrimidin-2-yl]heptanoic acid, ethanolamine salt, m.p. 137°;

7-[4-(3,4-methylenedioxybenzylamino)-5,6-cyclopenteno[1]benzothieno[2,3-d]pyrimidin-2-yl]heptanoic acid;

7-[4-(3,4-methylenedioxybenzylamino)-5,6-cyclohepteno[1]benzothieno[2,3-d]pyrimidin-2-yl]heptanoic acid;

7-[4-(3,4-methylenedioxybenzylamino)-6-methylthieno[2,3-d]pyrimidin-2-yl]heptanoic acid;

7-[4-(3,4-methylenedioxybenzylamino)-5,6-dimethylthieno[2,3-d]pyrimidin-2-yl]heptanoic acid;

7-[4-(3,4-methylenedioxybenzylamino)-6-ethylthieno[2,3-d]pyrimidin-2-yl]valeric acid;

7-[4-(3,4-methylenedioxybenzylamino)-6-chlorothieno[2,3-d]pyrimidin-2-yl]heptanoic acid;

2-{4-[4-(3-chloro-4-methoxybenzylamino)-5,6,7,8-tetrahydro[1]benzothieno[2,3-d]pyrimidin-2-yl]cyclohexyl}acetic acid;

2-{4-[4-(3-chloro-4-methoxybenzylamino)-6-ethylthieno[2,3-d]pyrimidin-2-yl]cyclohexyl}acetic acid;

2-{4-[4-(3,4-methylenedioxybenzylamino)-5,6,7,8-tetrahydro[1]benzothieno[2,3-d]pyrimidin-2-yl]cyclohexyl}acetic acid;

3-(4-benzylamino-5,6,7,8-tetrahydro[1]benzothieno[2,3-d]pyrimidin-2-yl]propionic acid, ethanolamine salt, m.p. 126°;

4-(4-benzylamino-5,6,7,8-tetrahydro[1]benzothieno[2,3-d]pyrimidin-2-yl) butyric acid, ethanolamine salt, m.p. 133°;

4-(4-benzylamino-5,6,7,8-tetrahydro[1]benzothieno[2,3-d]pyrimidin-2-yl]butyric acid, ethanolamine salt, m.p. 133°;

5-(4-benzylamino-5,6,7,8-tetrahydro[1]benzothieno[2,3-d]pyrimidin-2-yl]valeric acid, ethanolamine salt, m.p. 135°;

4-[4-benzylamino-6-methylthieno[2,3-d]pyrimidin-2-yl]butyric acid, ethanolamine salt, m.p. 165°;

5-[4-benzylamino-6-ethylthieno[2,3-d]pyrimidin-2-yl]valeric acid, ethanolamine salt, m.p. 162°.

EXAMPLE 3

1 equivalent of 3-[4-(3-chloro-4-methoxybenzylamino)-5,6,7,8-tetrahydro[1]benzothieno-[2,3-d]pyrimidine-2-yl]propionic acid and 1.2 equivalents of thionyl chloride are stirred in dichloromethane for 2 hours. The solvent is removed and 3-[4-(3-chloro-4-methoxybenzylamino)-5,6,7,8-tetrahydro[1]benzothieno[2,3-d]pyrimidine-2-yl]propionyl chloride is obtained. This is transferred to aqueous ammonia, the mixture is stirred for one hour and, after customary working up, 3-[4-(3-chloro-4-methoxybenzylamino)-5,6,7,8-tetrahydro[1]benzothieno[2,3-d]pyrimidine-2-yl]propionamide is obtained.

EXAMPLE 4

1 equivalent of DMF and 1 equivalent of oxalyl chloride are dissolved in acetonitrile at 0°. 1 equivalent of 3-[4-(3-chloro-4-methoxybenzylamino)-5,6,7,8-tetrahydro[1]benzothieno[2,3-d]pyrimidine-2-yl]propionamide is then added. The mixture is stirred for one hour. After customary working up, 3-[4-(3-chloro-4-methoxybenzylamino)-5,6,7,8-tetrahydro[1]-benzothieno[2,3-d]pyrimidine-2-yl]propionitrile is obtained.

EXAMPLE 5

The compounds below are obtained analogously to Examples 1 and 2

6-[4-(3-chloro-4-methoxybenzylamino)-5,6,7,8-tetrahydro[1]benzothieno[2,3-d]pyrimidin-2-yl]hexanoic acid, m.p. 165°;

2-[4-(3-chloro-4-methoxybenzylamino)-5,6,7,8-tetrahydro[1]benzothieno[2,3-d]pyrimidin-2-yl]propionic acid, ethanolamine salt, m.p. 150°;

4-[4-(3-chloro-4-methoxybenzylamino)-5,6,7,8-tetrahydro[1]benzothieno[2,3-d]pyrimidin-2-yl]-2,2-dimethylbutyric acid, ethanolamine salt, m.p. 130°;

4-[4-(3,4-methylenedioxybenzylamino)-5,6,7,8-tetrahydro[1]benzothieno[2,3-d]pyrimidin-2-yl]-2,2-dimethylbutyric acid, ethanolamine salt, m.p. 126°;

5-[4-(3-chloro-4-hydroxybenzylamino)-5,6,7,8-tetrahydro[1]benzothieno[2,3-d]pyrimidin-2-yl]valeric acid, m.p. 179°;

5-[4-(3,4-dichlorobenzylamino)-5,6,7,8-tetrahydro[1]benzothieno[2,3-d]pyrimidin-2-yl]valeric acid, ethanolamine salt, m.p. 136°;

5-[4-(3-chloro-4-isopropyloxybenzylamino)-5,6,7,8-tetrahydro[1]benzothieno[2,3-d]pyrimidin-2-yl]valeric acid, ethanolamine salt, m.p. 118°;

2-[4-(4-(3-chloro-4-methoxybenzylamino)-5,6,7,8-tetrahydro[1]benzothieno[2,3-d]pyrimidin-2-yl)phenyl]acetic acid, ethanolamine salt, m.p. 119°;

2-[4-(4-(3,4-methylenedioxybenzylamino)-5,6,7,8-tetrahydro[1]benzothieno[2,3-d]pyrimidin-2-yl)phenyl]acetic acid, m.p. 214.

The following examples relate to pharmaceutical preparations:

Example A

Injection Vials

A solution of 100 g of an active compound of the formula I and 5 g of disodium hydrogenphosphate is adjusted to pH 6.5 with 2 N hydrochloric acid in 3 l of double-distilled water, sterile filled, dispensed into injection vials, lyophilized under sterile conditions and aseptically sealed. Each injection vial contains 5 mg of active compound.

Example B

Suppositories

A mixture of 20 g of active compound of the formula I is fused with 100 g of soya lecithin and 1400 g of cocoa butter, poured into moulds and allowed to cool. Each suppository contains 20 mg of active compound.

Example C

Solution

A solution is prepared from 1 g of an active compound of the formula I, 9.38 g of $NaH_2PO_4.2H_2O$, 28.48 g of $Na_2HPO_4.12H_2O$, and 0.1 g of benzalkonium chloride in 940 ml of double-distilled water. The mixture is adjusted to pH 6.8, made up to 1 l and sterilized by irradiation. This solution can be used in the form of eye drops.

Example D

Ointment 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed in a customary manner to give tablets, such that each tablet contains 10 mg of active compound.

Example F

Coated Tablets

Analogously to Example E, tablets are pressed, which are then coated in a customary manner with a coating of sucrose, potato starch, talc, tragacanth and colourant.

Example G

Capsules 2 kg of active compound of the formula I are dispensed into hard gelatin capsules in a customary manner, such that each capsule contains 20 mg of the active compound.

Example H

Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

Example I

Inhalation Spray 14 g of active compound of the formula I are dissolved in 10 l of isotonic NaCl solution and the solution is dispensed into commercially available spray containers having a pump mechanism. The solution can be sprayed into the mouth or the nose. One burst of spray (approximately 0.1 ml) corresponds to a dose of approximately 0.14 mg.

What is claimed is:

1. A method for therapy and/or treatment of a disorder of the cardiovascular system, which comprises administering to a patient an effective amount of a compound of the formula I

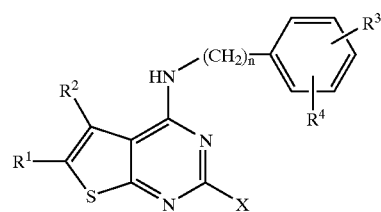

in which:

$R^1$ and $R^2$ in each case independently of one another, are H, A or Hal, where at least one of the radicals $R^1$ or $R^2$ is not H, or, optionally $R^1$ and $R^2$ together are alkylene having 3–5 C atoms;

$R^3$ and $R^4$ in each case independently of one another are H, A, OA or Hal, or, optionally, $R^3$ and $R^4$ together are alkylene having 3–5 C atoms, $—O—CH_2—CH_2—$, $—O—CH_2—O—$ or $—O—CH_2—CH_2—O—$, X is $R^5$ or $R^6$, which is monosubstituted by $R^7$;

$R^5$ is linear or branched alkylene having 1–10 C atoms, in which one or two $CH_2$ groups are optionally replaced by $—CH=CH—$ groups, or is $—C_6H_4—(CH_2)_m$;

$R^6$ is cycloalkylalkylene having 6–12 C atoms;

$R^7$ is COOH, COOA, $CONH_2$, CONHA, $CON(A)_2$ or CN;

A is alkyl having 1 to 6 C atoms;

Hal is F, Cl, Br or I;

m is 1 or 2; and n is 1, 2, or 3;

and/or a physiologically acceptable salt thereof.

2. The method of claim 1 wherein the compound of formula I is:

(a) 3-[4-(3-chloro-4-methoxybenzylamino)-5,6,7,8-tetrahydro[1]benzothieno[2,3-d]pyrimidin-2-yl]-propionic acid;

(b) 4-[4-(3,4-methylendioxybenzylamino)-5,6,7,8-tetrahydro[1]benzothieno[2,3-d]pyrimidin-2-yl]-butyric acid;

(c) 7-[4-(3,4-methylendioxybenzylamino)-5,6,7,8-tetrahydro[1]benzothieno[2,3-d]pyrimidin-2-yl]-heptanoic acid;

(d) 7-[4-(3-chloro-4-methoxybenzylamino)-5,6,7,8-tetrahydro[1]benzothieno[2,3-d]pyrimidin-2-yl]-heptanoic acid;

(e) 5-[4-(3-chloro-4-methoxybenzylamino)-5,6,7,8-tetrahydro[1]benzothieno[2,3-d]pyrimidin-2-yl]-valeric acid;

(f) 5-[4-(3-chloro-4-methoxybenzylamino)-6-methylthieno-[2,3-d]-pyrimidin-2-yl]valeric acid;

(g) 4-[4-(3-chloro-4-methoxybenzylamino)-6-methylthieno-[2 3-d]-pyrimidin-2-yl]butyric acid;

(h) 4-[4-(3,4-methylendioxybenzylamino)-6-methylthieno[2,3-d]pyrimidin-2-yl]butyric acid;

(i) 2-{4-(4-(3-chloro-4-methoxybenzylamino)-5,6,7,8-tetrahydro-[1]-benzothieno[2,3-d]pyrimidin-2-yl)-cyclohexyl-1-yl}acetic acid;

(k) 5-[4-(3,4-methylendioxybenzylamino)-6-methylthieno[2,3-d]pyrimidin-2-yl]valeric acid;

or a physiologically acceptable salt thereof.

3. The method of claim 1 wherein the compound of the formula I and/or one of its physiologically acceptable salts is provided in a dose of 1 to 500 mg.

4. The method of claim 1, wherein the compound of the formula I and/or a physiologically acceptable salt thereof is administered in a daily dose of 0.02 to 10 mg/kg of the patient's body weight.

5. The method of claim 1 wherein, the compound of the formula I and/or a physiologically acceptable salt thereof is administered orally.

6. The method of claim 1 wherein, in the compound of formula I, one of $R^1$ or $R^2$ is hydrogen and the other is ethyl, methyl, propyl or butyl, or $R^1$ and $R^2$ together are propylene, butylene or pentylene.

7. The method of claim 1, wherein in the compound of formula I, $R^7$ is COOH, COOCH$_3$, COOC$_2$H$_5$, CONH$_2$, CON(CH$_3$)$_2$, CONHCH$_3$ or CN.

8. The method of claim 1, wherein in the compound of formula I, $R^7$ is COOH or COOA.

9. The method of claim 1, wherein in the compound of formula I, $R^1$ and $R^2$ in each case independently of one another are H, A or Hal, where at least one of the radicals $R^1$ and $R^2$ is not H, and $R^7$ is COOH or COOA.

10. The method of claim 1, wherein, in the compound of formula I, $R^1$ and $R^2$ in each case independently of one another are H, A or Hal, where at least one of the radicals $R^1$ and $R^2$ is H, $R^7$ is COOH or COOA, and n is 1 or 2.

11. The method of claim 1, wherein, in the compound of formula I, $R^1$ and $R^2$ in each case independently of one another are H, A or Hal, where at least one of the radicals $R^1$ and $R^2$ is not H, or $R^1$ and $R^2$ together are alkylene having 3–5 C atoms, $R^3$ and $R^4$ in each case independently of one another are H, S, OA or Hal, or $R^3$ and $R^4$ together are —O—CH$_2$—O—, X is $R^5$ is linear or branched alkylene having 1 to 10 C atoms, or —C$_6$H$_4$—CH$_2$—, $R^7$ is COOH or COOA, m is 1 and n is 1 or 2.

12. The method of claim 1, wherein, in the compound of formula I, one of $R^1$ or $R^2$ is hydrogen and the other is A or Hal.

* * * * *

UNITED STATES PATENT AND TRADEMARK OFFICE
CERTIFICATE OF CORRECTION

PATENT NO. : 6,495,554 B2
DATED : December 17, 2002
INVENTOR(S) : Jonas et al.

It is certified that error appears in the above-identified patent and that said Letters Patent is hereby corrected as shown below:

Title page,
Item [30], Foreign Application Priority Data, delete "187 52 952" and insert -- 197 52 952 --.

Signed and Sealed this

Twenty-second Day of June, 2004

JON W. DUDAS
*Acting Director of the United States Patent and Trademark Office*